(12) United States Patent
Sweitzer

(10) Patent No.: US 12,241,502 B2
(45) Date of Patent: Mar. 4, 2025

(54) TOOL DRIVE ASSEMBLY

(71) Applicant: Shukla Medical, St. Petersburg, FL (US)

(72) Inventor: Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 215 days.

(21) Appl. No.: 17/301,943

(22) Filed: Apr. 20, 2021

(65) Prior Publication Data

US 2021/0324901 A1 Oct. 21, 2021

Related U.S. Application Data

(60) Provisional application No. 63/013,024, filed on Apr. 21, 2020.

(51) Int. Cl.
| | | |
|---|---|---|
| *A61B 17/16* | (2006.01) | |
| *B25B 23/00* | (2006.01) | |
| *B25F 5/02* | (2006.01) | |
| *F16C 1/06* | (2006.01) | |

(52) U.S. Cl.
CPC ............ *F16C 1/06* (2013.01); *A61B 17/1631* (2013.01); *B25B 23/0021* (2013.01); *B25F 5/026* (2013.01); *B25B 23/0028* (2013.01)

(58) Field of Classification Search
CPC ... F16C 1/06; A61B 17/1631; B25B 23/0021; B25B 23/0028; B25F 5/026
USPC .................................. 81/57.43, 58.1; 464/52
See application file for complete search history.

(56) References Cited

U.S. PATENT DOCUMENTS

| | | | | |
|---|---|---|---|---|
| 46,166 A | * | 1/1865 | Welham | 464/52 |
| 1,983,426 A | * | 12/1934 | Wise | B25B 13/461 |
| | | | | 81/58.1 |
| 2,663,336 A | * | 12/1953 | Sigvathsen | F16C 1/06 |
| 2,790,292 A | * | 4/1957 | Trecker | A01D 34/001 |

(Continued)

FOREIGN PATENT DOCUMENTS

| | | |
|---|---|---|
| EP | 3741512 A1 | 11/2020 |
| GB | 2446223 B1 | 8/2008 |
| KR | 100964472 B1 | 6/2010 |

OTHER PUBLICATIONS

Hikoki: "HIKOKI Winkelschraubvorsatz : Amazon.de: Baumarkt," http://www.amazon.de/hitachi-40018011-Winkelschraubvorsatz/dp/B01BD7HLAK/ref=pd_sbs_28/257-8033263-1346027?pd_rd_w=La7Jb&pf_rd_p=32abab06-7fd2-2b2e-a0f6-70b741a30b97&pf_rd_r=HYJ292PM0JTMQ0N55Z4G&pd_rd_r=06c489a6-bd40-4d5d-be58-fb767ca1965d&pd_rd_wg=DPxrZ&pd_rd_i=B01BD7HLAK&psc=1 [retrieved Sep. 13, 2021].

(Continued)

*Primary Examiner* — Greg Binda
(74) *Attorney, Agent, or Firm* — Kim IP Law Group LLC

(57) ABSTRACT

A tool drive assembly including a flexible drive shaft and a guide. The flexible drive shaft includes a proximal end structured to engage a driver for rotating the flexible drive shaft, and a distal end opposite the proximal end. The guide includes a handle, a shaft extending from the handle, and a hub assembly at a distal end of the shaft. The hub assembly includes a housing, and a hub rotatably mounted within the housing. The hub includes an input connection structured to attach to the distal end of the flexible drive shaft, and an output connection structured to attach to a working tool. The tool drive assembly enables easy manipulation and driving of a working tool to achieve optimum positioning and effectiveness of the working tool.

16 Claims, 7 Drawing Sheets

(56) References Cited

U.S. PATENT DOCUMENTS

| | | | | |
|---|---|---|---|---|
| 3,146,576 | A | * | 9/1964 | Wezel ............... B21F 45/06 |
| 4,545,395 | A | * | 10/1985 | Kolb ............... B44D 3/006 |
| 4,546,676 | A | * | 10/1985 | Kiefer, Jr. ............... B25B 13/48 |
| | | | | 81/58.1 |
| 2019/0270187 | A1 | | 9/2019 | Chiang |

OTHER PUBLICATIONS

Wera: "Wera 5003642001 8796 SC Cyclop Extension Flexible Lock with Quick Turn Sleeve, Short, 1/2 Inch x 125.0 mm, 125 mm : Amazon.de: Baumarkt" http://www.amazon.de/Wera-05003642001-Zyklop-Verlängerung-Flexible-Lock-Schnelldrehhusle/dp/B003GDIS0W/ref-asc_df_B003GDIS0W/?tag=googshopde-21&linkcode-df0&hvadid=256220659813&hvpos=&hvnetw=g&hvrand=5841959075671733861&hvpone=&hvptwo=&hvqmt=&hvdev=c&hvdvcmdl=&hvlocint=&hvlocphy=1004234&hvtargid=pl [retrieved Sep. 14, 2021.

Partial European Search Report for EP 21169500.2; issued Sep. 22, 2021.

Extended European search report dated Jan. 19, 2022 in European application No. 21169500.2.

Eyech: "Eyech 0.3-6.5mm Flex Shaft Extension Chuck Key Flexible Shaft Power Drill Converter Attachment", May 21, 2019 (May 21, 2019), XP055877477, Retrieved from the Internet: URL:https://www.amazon.com/Eyech-0-3-6-5mm-Extension-Attachment-Woodworking/dp/B07S5RNH58 [retrieved on Jan. 11, 2022].

\* cited by examiner

TOOL DRIVE ASSEMBLY

CROSS-REFERENCE TO RELATED APPLICATION

This application claims the benefit under 35 U.S.C. § 119(e) to U.S. Provisional Application No. 63/013,024, filed Apr. 21, 2020, and entitled "Flexshaft and Guide," the entire disclosure of which is hereby incorporated by reference for all purposes.

BACKGROUND OF THE DISCLOSURE

The exemplary embodiments of present invention relate generally to tool drive assemblies and, more specifically, to a tool drive assembly comprising a tool guide and a flexible drive shaft for driving a working tool.

An example of a typical tool drive would be a rigid linear shaft providing torque to drive a fastener or bone screw in the clockwise or counter clockwise direction, wherein the shaft is powered via hand or a power tool such as a drill. In certain applications, e.g., an orthopedic revision surgery, access to the surgical site can be very limited. Often there is soft tissue or bone that obstructs or prohibits a rigid linear shaft to reach the desired location. As a result, a typical tool drive arrangement may not fit within the surgical site or incision. A flexible drive shaft and a guide in accordance with the subject disclosure offers a solution to this problem in that it allows the user to steer the driver tip into tight areas.

BRIEF SUMMARY OF THE DISCLOSURE

In accordance with an exemplary embodiment there is provided a tool drive assembly that includes a flexible drive shaft and a guide. The flexible drive shaft includes a proximal end structured to engage a driver for rotating the flexible drive shaft, and a distal end opposite the proximal end. The guide comprises a handle, a guide shaft extending from the handle, and a hub assembly at a distal end of the guide shaft. The hub assembly includes a housing, and a hub mounted within the housing. The hub includes an input connection structured to engage the distal end of the flexible drive shaft, and an output connection structured to engage a working tool.

According to an aspect, the flexible drive shaft comprises a series of wound wires in alternating directions forming layers and a flexible sleeve covering the series of wound wires. According to another aspect, the distal end of the flexible drive shaft includes a female connector.

According to an aspect, a longitudinal axis of the housing portion is coaxial with a longitudinal axis of the hub. According to another aspect, the hub assembly further comprises a bearing between the hub and the housing for rotation of the hub relative to the housing. According to another aspect, the guide shaft extends from the housing at an angle of about 20-60 degrees relative to a central longitudinal axis of the housing.

According to an aspect, the input connection is a male connector, and the output connection is a female connector. According to another aspect, the input connection is a square male connector and the output connection is a female socket.

In accordance with another exemplary embodiment there is provided a tool drive assembly comprising a flexible drive shaft and a guide. The flexible drive shaft comprises a series of wound wires wrapped in alternating directions forming layers and a flexible sleeve covering the series of wound wires. The flexible drive shaft includes a proximal end having a male connector for engaging a driver for rotating the flexible drive shaft, and a distal end having a female connector. The guide comprises a guide shaft, and a hub assembly at a distal end of the shaft. The hub assembly includes a housing having a substantially cylindrical housing portion and a laterally extending mount connected or connectable to the guide shaft. The guide shaft extends from a central longitudinal axis of the housing at an angle of about 20-60 degrees. The hub assembly further includes a hub rotatably mounted within the housing. The hub has a male input connection for operatively engaging the female connector of the flexible drive shaft, a female output connection for operatively engaging a working tool, and a bearing disposed between the hub and the housing.

In accordance with another exemplary embodiment there is provided a tool drive assembly comprising a flexible drive shaft and a guide assembly. The flexible drive shaft includes a proximal end structured to engage a driver for rotating the flexible drive shaft, and a distal end opposite the proximal end. The guide assembly comprises a handle having a guide shaft, and a first hub assembly including a first housing having a substantially cylindrical housing portion and a laterally extending mount connectable to the guide shaft at a first angle relative to a central longitudinal axis of the first housing. The first hub assembly further includes a first hub mounted within the first housing, the first hub having a first input connection structured to engage the distal end of the flexible guide shaft, and a first output connection structured to engage a working tool. The guide assembly further comprises a second hub assembly including a second housing having a substantially cylindrical housing portion and a laterally extending mount connectable to the guide shaft at a second angle relative to a central longitudinal axis of the second housing, wherein the second angle is greater than the first angle. The second hub assembly further includes a second hub mounted within the second housing, the second hub having a second input connection structured to engage the distal end of the flexible guide shaft, and a second output connection structured to engage the working tool.

The foregoing exemplary embodiments of the subject disclosure provide a tool drive assembly for easily manipulating and driving a working tool to achieve optimum positioning and effectiveness of the working tool.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DETAILED DESCRIPTION OF THE DISCLOSURE

Figure 1:
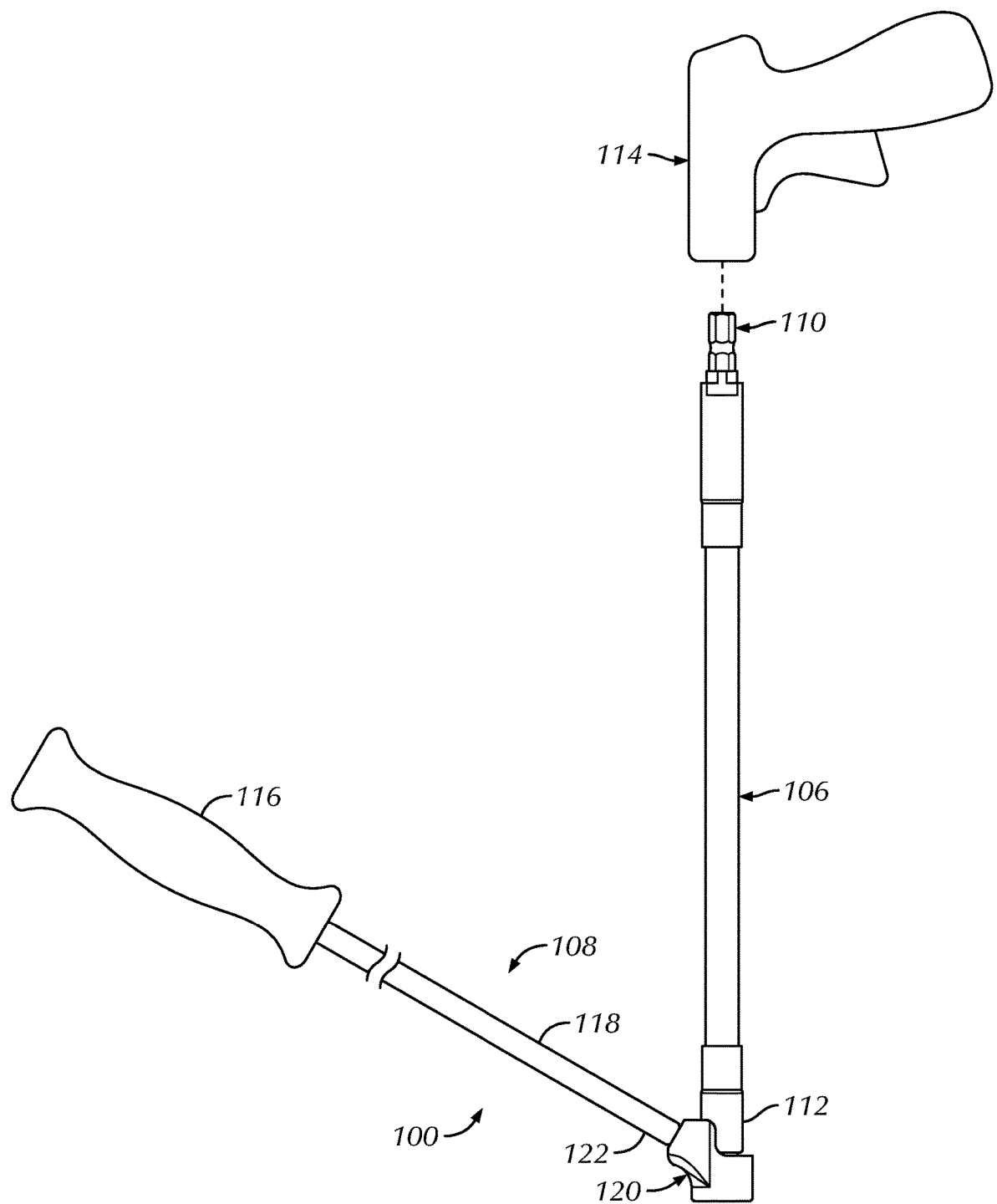
FIG. 1 is side view of a tool drive assembly in accordance with an exemplary embodiment of the subject disclosure.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 2:
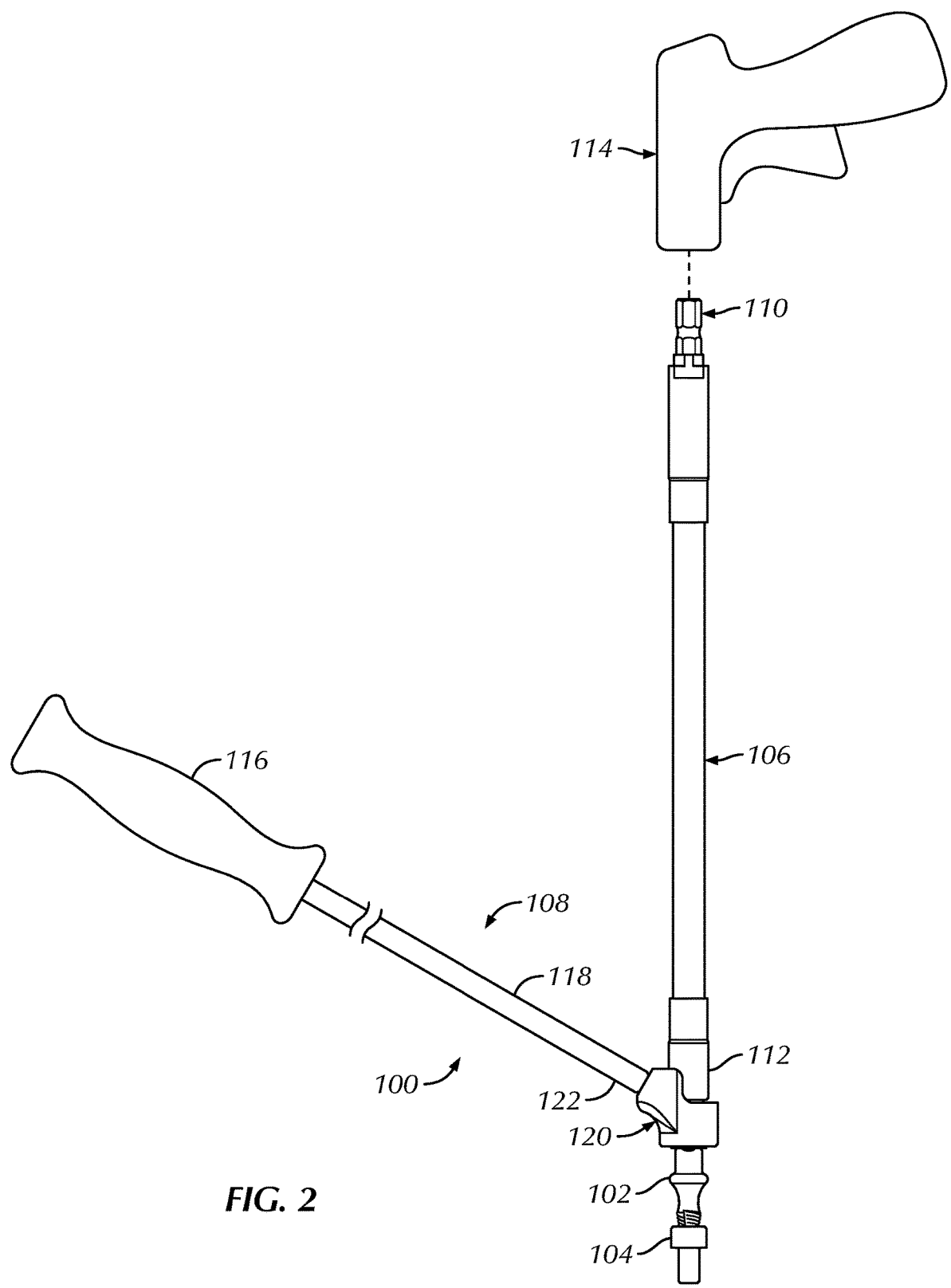
FIG. 2 is a view of the tool drive assembly of FIG. 1 with a working tool attached thereto.

Referring to the drawings, FIGS. 1 and 2 illustrate a tool drive assembly 100 in accordance with an exemplary embodiment of the present disclosure. FIG. 2 illustrates the tool drive assembly 100 connected to a working tool 102. The working tool can be, e.g., a drill bit, a broken screw extractor or, as illustrated, a stripped screw extractor for extracting a stripped screw 104 from an unillustrated substrate. By way of example, but not limitation, screw 104 can be a bone screw and the unillustrated substrate can be bone.

The tool drive assembly 100 comprises a flexible drive shaft 106 and a guide 108. The flexible drive shaft includes a proximal end 110 and a distal end 112 opposite the proximal end. The proximal end 110 of the flexible drive shaft 106 may be constructed, for example, as a Hudson connection or other suitable connection that is structured to engage a driver 114 such as a pneumatic drill, a hydraulic drill or a corded or cordless electric drill. The guide 108 comprises a handle 116, a shaft 118 extending from the handle and a hub assembly 120 at a distal end 122 of the shaft.

FIGS. 3A-3D illustrate various features of the hub assembly 120. The hub assembly 120 comprises a housing 124 and a hub 126 rotatably mounted within the housing. The housing includes a cylindrical housing portion 128 and the hub is mounted within the cylindrical housing portion. A longitudinal axis "A" of the cylindrical housing portion is coaxial with a longitudinal axis "B" of the hub.

The housing further includes a laterally extending mount 130 connected to the shaft 118. The mount 130 includes a mounting face 131 having an angle of about 20 to 60 degrees including, e.g., 15, 25, 30, 35, 40, 45, 50, 55, 65, 70 and 75 degrees, relative to the longitudinal axis A of the cylindrical housing portion. The mount also includes a recess 133 for receiving a fastening tip of the shaft 118. The recess is spaced from the distal end of the hub, e.g., above the socket counterbore or above the bearings 136, 136'. The shaft 118 may be releasably or fixedly connected to the mounted 130. If releasably connected, the recess 133 can be configured to include threads or a detent to attach a correspondingly threaded or notched fastening tip of the shaft in the recess. If fixedly connected, the fastening tip of the shaft 118 can be welded in the recess. The shaft 118 is a rigid shaft which can be formed out of a metal or rigid polymer. That is, the rigid shaft can be a non-flexible shaft.

Figure 3A:
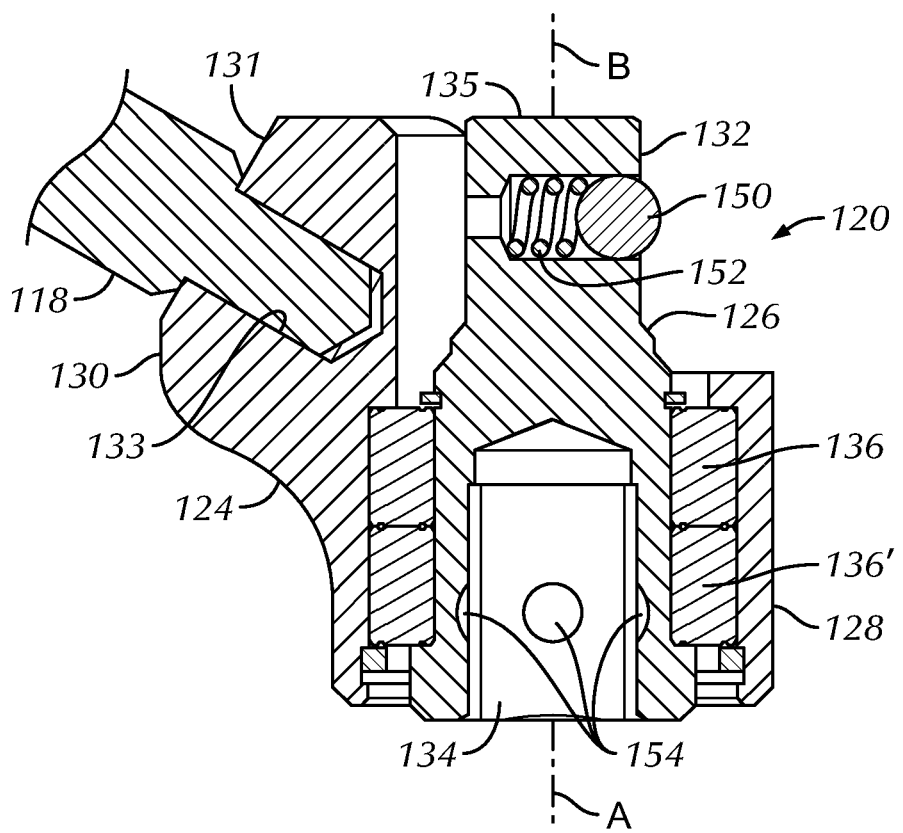
FIG. 3A is a cross-sectional side view of a hub assembly of the tool drive assembly of FIG. 1.
Figure 3B:
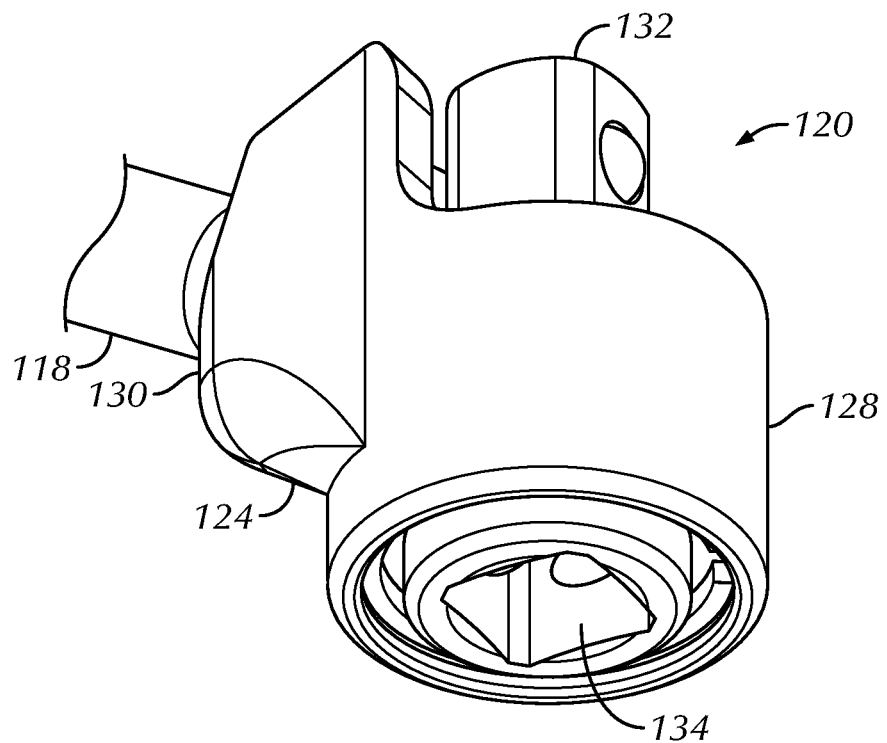
FIG. 3B is a bottom perspective view of the hub assembly of FIG. 3A.
Figure 3C:
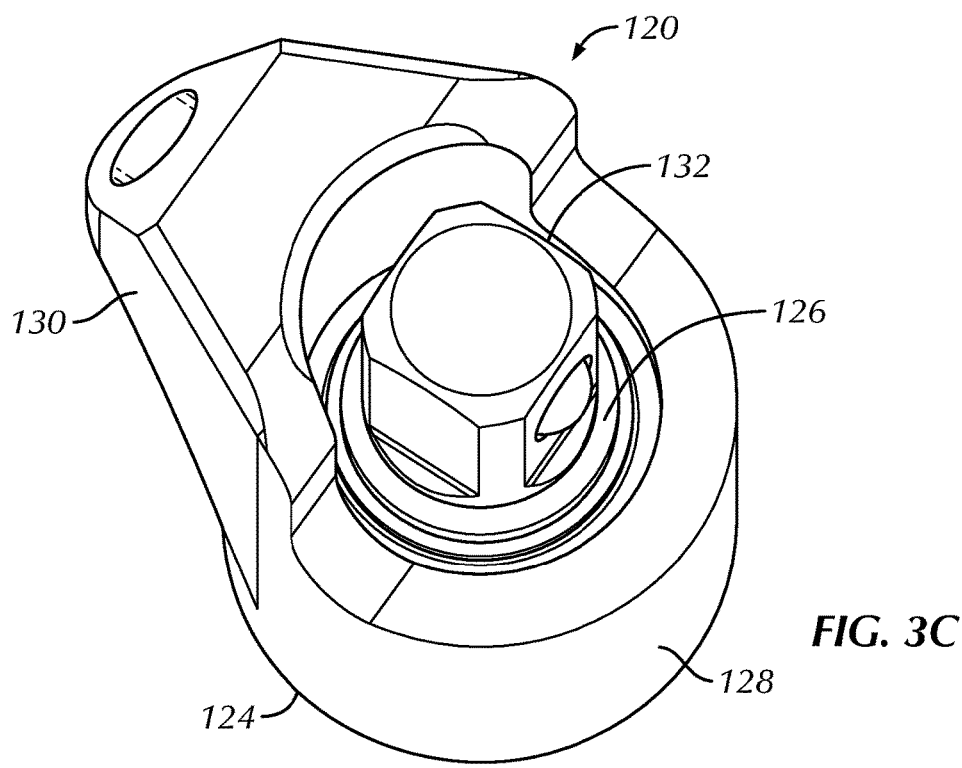
FIG. 3C is an enlarged top perspective view of the hub assembly of FIG. 3A.
Figure 3D:
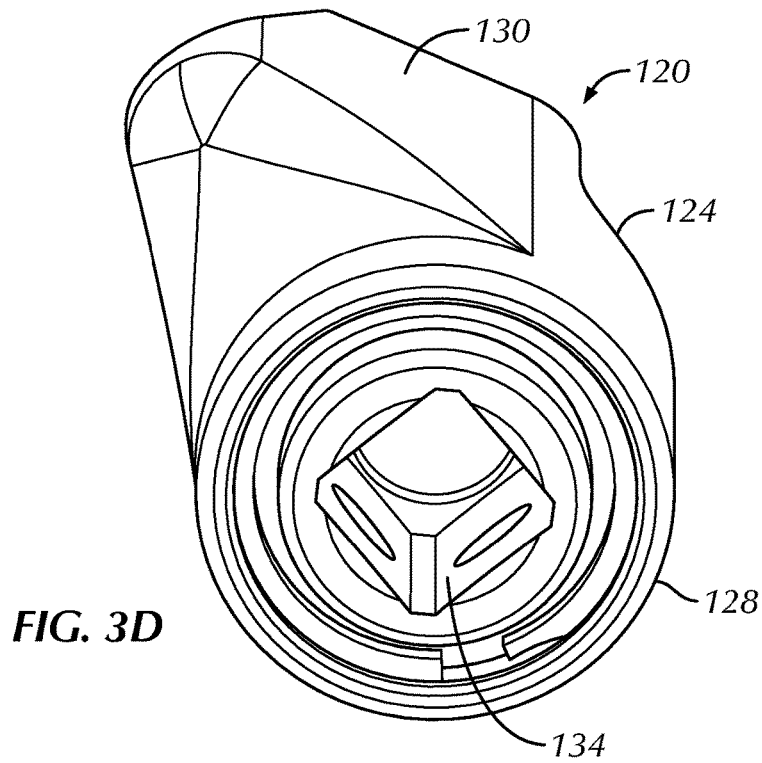
FIG. 3D is an enlarged bottom perspective view of the hub assembly of FIG. 3A.

The hub 126 includes an input connection 132 structured to attach to or engage the distal end 112 of the flexible drive shaft 106. The input connection extends upwardly or proximally along the direction of its longitudinal axis and has a proximally facing face 135. According to an aspect, the input connection 132 is configured as a male connector. According to a further aspect, the input connection is structured to have a polygonal shaped longitudinal cross-section and may alternatively be configured, without limitation, to have the shape of a square male connector or other suitable shape. As best shown in FIG. 3A, the input connection 132 includes a yieldable detent 150, e.g., a ball-type detent, which is biased outwardly by a suitable biasing means 152 such as a spring or an elastomer to enable the input connection to releasably but firmly engage the distal end 112 of the flexible drive shaft 106.

The hub further includes an output connection 134 structured to attach to or engage a working tool such as working tool 102. According to an aspect, the output connection 134 is a female connector, e.g., a female socket. According to a further aspect, the output connection has a polygonal shaped longitudinal cross-section and may alternatively be configured, without limitation, to have the shape of a square female socket or any other suitable shape. The output connection has an opening facing downwardly or distally, opposite the proximally facing face 135. A distal end of the output connection extends further than a most distal end of the cylindrical housing portion 128. Further, the walls of the output connection are provided with a least one recess 154 configured to releasably yet firmly receive an unillustrated detent provided on the working tool 102.

In addition to the foregoing, the hub assembly 120 further comprises a bearing 136 disposed between the hub 126 and the housing 124 to facilitate smooth rotation of the hub within the housing. The bearing 136 can be, e.g., an annular bearing, a bushing, a ball bearing and the like suitable for its intended purpose. The hub assembly can alternatively include more than one bearing e.g., a plurality of bearings 136, 136'.

Figures 4, 5, 6:
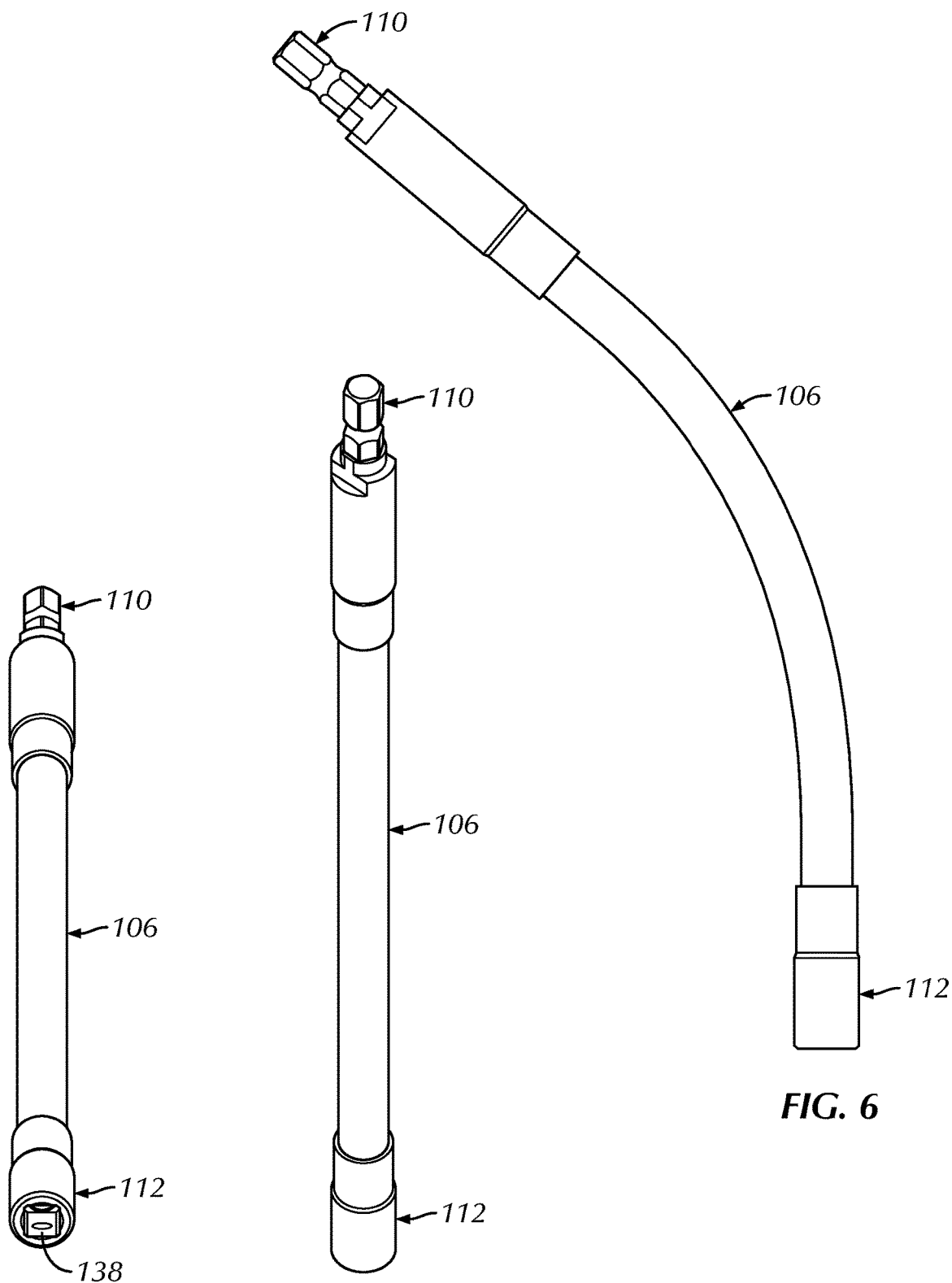
FIG. 4 is a front perspective view of a flexible drive shaft of the tool drive assembly of FIG. 1.
FIG. 5 is a rear perspective view of the flexible drive shaft of FIG. 4.
FIG. 6 is a side view of the flexible drive shaft of FIG. 4 in a flexed position.
Figure 7:
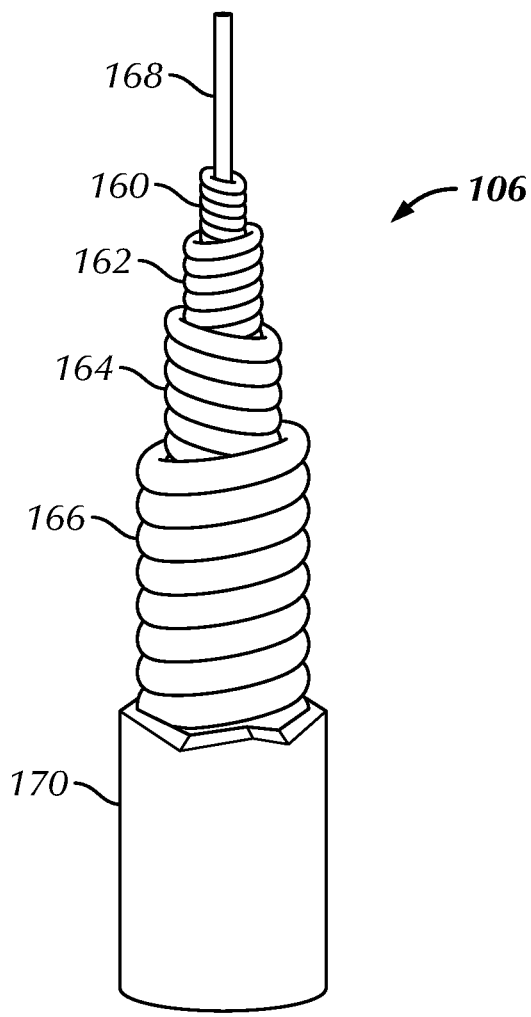
FIG. 7 is a cutaway view of an exemplary construction of the flexible guide shaft of FIG. 4.

FIGS. 4-7 illustrate various views of the flexible drive shaft 106. According to an exemplary embodiment as shown in FIG. 7, the flexible drive shaft comprises a series of alternating wound wires, e.g., 160, 162, 164, 166 surrounding a flexible mandrel 168 forming layers and covered by a flexible sleeve 170. The flexible sleeve may be fabricated from any suitable flexible material including, without limitation, a polymer e.g., silicone, an elastomer, or a metal, e.g., corrugated tubing and the like. FIG. 6 shows the proximal end 110 of the flexible drive shaft bent at an angle of about 45 degrees with respect to the distal end 112. The flexible drive shaft is structured sufficiently to allow bending or flexing between about 1 to 175 degrees, including 10, 20, 30, 40, 50, 60, 70, 80, 90, 100, 110, 120, 130, 140, 150, 160, and 170 degrees, to provide the user optimum maneuverability when manipulating the flexible drive shaft. Depending on the length of the drive shaft which can range from about 2 to 24 or more inches, including 3, 4, 6, 8, 10, 12, 14, 16, 18, 20, 22 and 25 inches, the drive shaft can be bent in an increasing degree of angle. For example, a very long shaft can be bent into a circle although such capability is not practical for most applications. An angle of 175 degrees is likely the maximum angle of bending but would be only needed in rare cases. More important is the effective radius of the bend. A shaft that can bend with a small radius typically compromises the torsional strength. Conversely, a shaft that can only bend with a large radius has exceptional torsional strength but compromises maneuverability. According to an exemplary embodiment, the flexible shaft is advantageously structured sufficiently to have a bend radius of about 1 inch to 6 inches, including 2, 3, 4 and 5 inches, and can withstand a torsional strength of about 50 to 400 inch-lbs. by optimizing the internal wire diameter, spacing between the wound internal wires, overall diameter, and wire material type used to form the flexible shaft. As used herein, a flexible shaft is defined as a shaft that is capable of bending without breaking or capable of being flexed.

As noted above, the proximal end 110 of the flexible drive shaft is structured to engage a driver such as driver 114. The distal end 112 of the flexible drive is structured to connect to the input connection 132 of the hub 126 to rotatably drive the hub. According to an aspect, the distal end of the flexible drive shaft includes a female connector 138 such as, for example, a square socket.

Figure 8A:
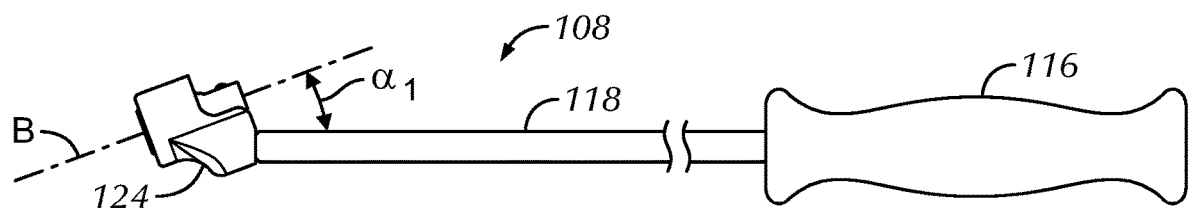
FIG. 8A is a side view of a guide of the tool drive assembly of FIG. 1 with the guide shaft extending at a first angle with respect to a longitudinal central axis of a shaft of the tool drive assembly.
Figure 8B:
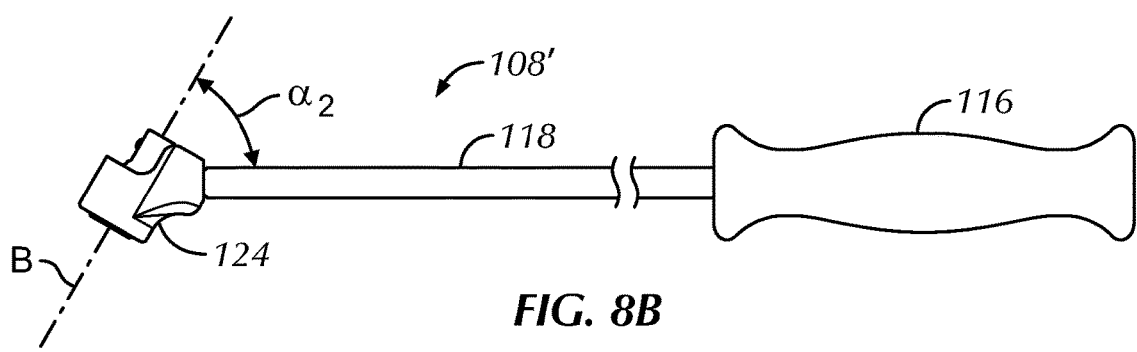
FIG. 8B is a side view of a guide of the tool drive assembly of FIG. 1 with the guide shaft extending at a second angle with respect to a longitudinal central axis of the shaft of the tool drive assembly, in accordance with another aspect of the present disclosure.

Referring to FIGS. 8A and 8B, there are shown two exemplary embodiments of the guide 108, 108' of the tool drive assembly according to the subject disclosure. As shown in FIG. 8A, the shaft 118 extends from a central longitudinal axis "B" of the hub housing 124 at an angle "$\alpha_1$" of about 20 degrees. As shown in FIG. 8B, the shaft 118' extends from a central longitudinal axis "B" of the hub housing 124' at an angle "$\alpha_2$" of about 60 degrees. It is understood that the angle of the shaft 118 with respect to the central longitudinal axis of the hub housing may be less than 20 degrees, between 20-60 degrees, and greater than 60 degrees including, e.g., 15, 25, 30, 35, 40, 45, 50, 55, 65, 70 and 75 degrees.

Referring to FIGS. 8A and 8B, according to an aspect, the tool drive assembly 100 according to the subject disclosure can comprise a kit including a guide assembly 108, 108' comprising a handle having a guide shaft 118, a first hub assembly including a first housing 124 having a substantially cylindrical housing portion and a laterally extending mount 130 connectable to the guide shaft 118 at a first angle $\alpha_1$ relative to a central longitudinal axis of the first housing. The first hub assembly further includes a first hub 126 mounted within the first housing 124, the first hub having a first input connection 132 structured to engage the distal end of the flexible guide shaft 118, and a first output connection 134 structured to engage a working tool 102. The guide assembly 108, 108' further comprises a second hub assembly including a second housing 124 having a substantially cylindrical housing portion and a laterally extending mount 130 connectable to the guide shaft 118 at a second angle $\alpha_2$ relative to a central longitudinal axis of the second housing, wherein the second angle is greater than the first angle. The second hub assembly further includes a second hub 126 mounted within the second housing 124, the second hub 126 having a second input connection 132 structured to engage the distal end of the flexible guide shaft 118, and a second output connection 134 structured to engage the working tool 102. Each of the laterally extending mounts 130 of the first and second housings 124, 124 include a recess or connection for releasably connecting to a distal end of the guide shaft 118.

Prior to operation, a user selects an appropriate guide 108, attaches the proximal end 110 of the flexible drive shaft 106 to the driver 114, attaches the distal end 112 of the flexible drive shaft to the input connection 132 of the hub 126, and attaches the working tool 102 to the output connection 134 of the hub. The user then grasps the handle 116 and moves the distal end of the guide to the region or object to be worked by the working tool. By way of example, but not limitation, the working tool can be a stripped screw extractor which is inserted into the stripped head of a screw to be extracted. While holding the guide in position, the user activates the driver 114 to rotate the flexible drive shaft 106, the hub 126 and the working tool 102 until the distal end of the working tool becomes embedded in the stripped head of the screw. The user then operates the driver to extract the screw from the substrate. Owing to the flexibility of the flexible drive shaft and the maneuverability of the guide, the user can comfortably move the tool drive assembly 100 to effectively operate the working tool to achieve a variety of ends including, without limitation, hole drilling, stripped screw extraction and broken screw extraction.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

I claim:

1. A tool drive assembly comprising:
 a flexible drive shaft that includes:
  a proximal end structured to engage a driver for rotating the flexible drive shaft, and
  a distal end opposite the proximal end; and
 a guide comprising:
  a handle,
  a guide shaft extending from the handle, and
  a hub assembly at a distal end of the guide shaft, the hub assembly including:
   a housing,
   a hub mounted within the housing, the hub having:
    an input connection having a detent for releasably engaging the distal end of the flexible drive shaft, and
    an output connection having a recess for engaging a working tool.

2. The tool drive assembly of claim 1, wherein the guide shaft extends from the housing at an angle of about 20-60 degrees relative to a central longitudinal axis of the housing.

3. The tool drive assembly of claim 1, wherein the hub assembly further comprises a bearing between the hub and the housing for rotation of the hub relative to the housing.

4. The tool drive assembly of claim 3, wherein the housing has a lateral recess.

5. The tool drive assembly of claim 4, wherein the lateral recess is above the bearing.

6. The tool drive assembly of claim 3, wherein the handle extends above the bearing.

7. The tool drive assembly of claim 1, wherein the distal end of the flexible drive shaft includes a female connector.

8. The tool drive assembly of claim 1, wherein the input connection is a male connector and the output connection is a female connector.

9. The tool drive assembly of claim 1, wherein the input connection is a square male connector and the output connection is a female socket.

10. The tool drive assembly of claim 1, wherein the flexible drive shaft comprises a series of wound wires wrapped in alternating directions forming layers.

11. The tool drive assembly of claim 10, wherein the flexible drive shaft comprises a flexible sleeve covering the series of wound wires.

12. The tool drive assembly of claim 1, wherein a longitudinal axis of the housing portion is coaxial with a longitudinal axis of the hub.

13. The tool drive assembly of claim 1, wherein the housing has a laterally extending mount connected or connectable to the guide shaft.

14. The tool drive assembly of claim 1, wherein the housing has a central longitudinal axis and a mounting face at an angle of about 20-60 degrees relative to the central longitudinal axis.

15. A tool drive assembly comprising:
 a flexible drive shaft comprising:
  a series of wound wires wrapped in alternating directions forming layers,
  a flexible sleeve covering the series of wound wires,
  a proximal end having a male connector for engaging a driver for rotating the flexible drive shaft, and
  a distal end having a female connector; and
 a guide comprising:
  a guide shaft, and
  a hub assembly at a distal end of the guide shaft, the hub assembly including:
   a housing having a substantially cylindrical housing portion and a laterally extending mount connected or connectable to the guide shaft, wherein the guide shaft extends from a central longitudinal axis of the housing at an angle of about 20-60 degrees,
   a hub rotatably mounted within the housing, the hub having:
    a male input connection for operatively engaging the female connector of the flexible drive shaft,
    a female output connection for operatively engaging a working tool, and
   a bearing disposed between the hub and the housing.

16. A tool drive kit comprising:
 a hand drill;
 a flexible drive shaft that includes:
  a proximal end structured to engage the hand drill, and
  a distal end opposite the proximal end; and
 a guide assembly comprising:
  a handle having a guide shaft; and
  a first hub assembly including:
   a first housing having a substantially cylindrical housing portion and a laterally extending mount connectable to the guide shaft at a first angle relative to a central longitudinal axis of the first housing, and
   a first hub mounted within the first housing, the first hub having:
    a first input connection structured to engage the distal end of the flexible guide shaft, and
    a first output connection structured to engage a working tool, and
  a second hub assembly including:
   a second housing having a substantially cylindrical housing portion and a laterally extending mount connectable to the guide shaft at a second angle relative to a central longitudinal axis of the second housing, wherein the second angle is greater than the first angle, and
   a second hub mounted within the second housing, the second hub having:
    a second input connection structured to engage the distal end of the flexible guide shaft having a proximal end configured to be operated by the user's second hand, and
    a second output connection structured to engage the working tool.

* * * * *